(12) United States Patent
Peeters et al.

(10) Patent No.: US 11,918,332 B2
(45) Date of Patent: Mar. 5, 2024

(54) INDUCTIVE SENSING DEVICE AND METHOD

(71) Applicant: KONINKLIJKE PHILIPS N.V., Eindhoven (NL)

(72) Inventors: Wouter Herman Peeters, Waalre (NL); Jacobus Josephus Leijssen, Waalre (NL); Gerardus Johannes Nicolaas Doodeman, Eindhoven (NL); Rick Bezemer, Eindhoven (NL); Mark Peter Paul Kleijnen, Eindhoven (NL); Ronny Hubertus Johannes Grosfeld, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 531 days.

(21) Appl. No.: 17/273,361

(22) PCT Filed: Aug. 28, 2019

(86) PCT No.: PCT/EP2019/072896
§ 371 (c)(1),
(2) Date: Mar. 4, 2021

(87) PCT Pub. No.: WO2020/048834
PCT Pub. Date: Mar. 12, 2020

(65) Prior Publication Data
US 2021/0321898 A1 Oct. 21, 2021

(30) Foreign Application Priority Data
Sep. 4, 2018 (EP) ...................................... 18192484

(51) Int. Cl.
*A61B 5/05* (2021.01)
*A61B 5/00* (2006.01)

(52) U.S. Cl.
CPC .............. *A61B 5/05* (2013.01); *A61B 5/7225* (2013.01)

(58) Field of Classification Search
CPC ........... A61B 5/05; A61B 5/242; A61B 5/248; A61B 5/7225; G01V 3/107
See application file for complete search history.

(56) References Cited

U.S. PATENT DOCUMENTS

| 2004/0113617 A1 | 6/2004 | de Swiet et al. |
| 2009/0306524 A1 | 12/2009 | Muhlsteff |
| 2015/0185294 A1 | 7/2015 | Reitsma |

FOREIGN PATENT DOCUMENTS

| CN | 101019006 A | 8/2007 |
| CN | 101444421 A | 6/2009 |

(Continued)

OTHER PUBLICATIONS

International Search Report and Written Opinion, International Application No. PCT/EP2019/072896, dated Aug. 28, 2019.

(Continued)

*Primary Examiner* — Boniface N Nganga

(57) ABSTRACT

An inductive sensing device comprises first (16) and second (24) loops, the first loop (16) being coupled with a capacitor to form a resonator circuit (20), and the resonator circuit and second loop being coupled via an active buffering component (28). The active buffering component provides voltage to current amplification, and an output of the buffering component drives a current in the second loop. Conductive lines forming each of the first and second loop parts are radially spaced apart.

15 Claims, 4 Drawing Sheets

(56) References Cited

FOREIGN PATENT DOCUMENTS

| KR | 2016034882 A | 3/2016 |
|---|---|---|
| WO | 2006016147 A2 | 2/2006 |
| WO | 2008015598 A2 | 2/2008 |
| WO | 2018127488 A1 | 7/2018 |

OTHER PUBLICATIONS

Shao, Q. et al., "Efficiency analysis and optimization of wireless power transfer system for freely moving biomedical implants", Technological Sciences, Jan. 2017, vol. 60, No. 1: 91-101.

Hart, L. W., Ko, H. W., Meyer, J. H., Vasholz, D. P., & Joseph, R. I. (1988). A noninvasive electromagnetic conductivity sensor for biomedical applications. IEEE Transactions on Biomedical Engineering, 35(12), 1011-1022.

Kwok, M., & Pepper, M. (1991). Noninvasive detection of ventricular wall motion by electromagnetic coupling Part 1: Theory. Medical and Biological Engineering and Computing, 29(2), 136-140.

Richer, a., & Adler, a. (2005). Eddy Current Based Flexible Sensor for Contactless Measurement of Breathing. 2005 IEEE Instrumentation and Measurement Technology Conference Proceedings, 1(May), 17-19.

Gi, S. O., Lee, Y. J., Koo, H. R., Khang, S., Kim, K. N., Kang, S. J., . . . Lee, J. W. (2015). Application of a textile-based inductive sensor for the vital sign monitoring. Journal of Electrical Engineering and Technology, 10(1), 364-371.

Teichmann, D., Foussier, J., Jia, J., Leonhardt, S., & Walter, M. (2013). Noncontact monitoring of cardiorespiratory activity by electromagnetic coupling. IEEE Transactions on Biomedical Engineering, 60(August), 2142-2152.

Guardo, R., Charron, G., Goussard, Y., & Savard, P. (1997). Contactless measurement of thoracic conductivity changes by magnetic induction. Proc. 19th Int. Conf. IEEE Eng. in Med. and Biol., 2450(C), 2450-2453.

Tarjan, P. P., & McFee, R. (1968). Electrodeless measurements of the effective resistivity of the human torso and head by magnetic induction. IEEE Transactions on Bio-Medical Engineering, 15(Oct. 1968), 266-278.

Igney, C. H. H., Watson, S., Williams, R. J. J., Griffiths, H., & Dossel, O. (2005). Design and performance of a planar-array MIT system with normal sensor alignment. Physiological Measurement, 26, S263-S278.

Griffiths, H., Stewart, W. R., & Cough, W. (1999). Magnetic induction tomography. A measuring system for biological tissues. Annals of the New York Academy of Sciences.

Scharfetter, H., & Merwa, R. (2007). 13th International Conference on Electrical Bioimpedance and the 8th Conference on Electrical Impedance Tomography : ICEBI 2007, Aug. 29-Sep. 2, 2007, Graz, Austria. IFMBE Proceedings, (Jan. 2017).

INDUCTIVE SENSING DEVICE AND METHOD

This application is the U.S. National Phase application under 35 U.S.C. § 371 of International Application No. PCT/EP2019/072896, filed on 28 Aug. 2019, which claims the benefit of European Application Serial No. 18192484.6, filed 4 Sep. 2018. These applications are hereby incorporated by reference herein.

FIELD OF THE INVENTION

The invention relates to an inductive sensing device for coupling electromagnetic signals into and out of a medium.

BACKGROUND OF THE INVENTION

Inductive sensing can be used as a means of non-invasive investigation of properties of a body.

In one advantageous area of application, inductive sensing can be used as a means of non-invasively investigating physiological characteristics, in particular heart and lung dynamics. Inductive sensing is based on magnetic induction and has several advantages over conductive and capacitive sensing.

An advantage compared to conductive sensing, such as bio-impedance measurements, is that adhesive electrodes are not required; sensing may be performed without contact and/or through non-conductive material, such as textile and plastic. In addition, inductive sensing signals are significantly less susceptible to corruption by motion artifacts.

An advantage compared with capacitive sensing is that inductive sensing is based on magnetic fields rather than electric fields and as a result is more sensitive to changes at greater penetration depth inside the body, as opposed to those just occurring at skin level. This is because magnetic fields penetrate deeper into a body than electrical fields, and thus magnetic fields can be used to measure changes in properties deeper inside the body, whereas electrical fields are predominantly useful only for measuring effects at the surface of the skin such as changes in skin properties (e.g. permittivity) or movement of the skin (skin proximity).

Coil-based inductive sensors function by inductively coupling with electromagnetic signals (i.e. electromagnetic waves or oscillations), wherein propagation of the signals through the coil leads to a change in the current through the coil, which can be measured and used to sense properties of the propagated signal (including e.g. frequency spectrum, amplitude and phase pattern).

An electromagnetic excitation signal can be propagated into a body to be investigated. The excitation electromagnetic signal causes magnetic induction in the body, i.e. the generation of eddy currents in the tissue of the body due to the application of an external magnetic field. These eddy currents then in turn generate electromagnetic signals propagated out of the body which interact with the applied fields in a way that allows them to be sensed by the coil.

Movements of tissue in the body can manifest in changes in volumes of local regions of the tissue and in changes of the conductive or dielectric properties of a tissue. These changes then cause amplitude and/or phase modulations of the electromagnetic signal which are emitted out of the body in response to the electromagnetic stimulation. By monitoring these changes, movement and size change of elements within the body can be detected and tracked, and changes in the conductivity and dielectric properties can be tracked. For example, heart contractions manifest themselves mainly as movement of blood, and breathing mainly manifests itself as changes in the conductivity of the lung.

The received signals can be sensed in a quantitative way by measuring an oscillating or resonating frequency of the transmitting coil.

There are two main known approaches to sensing the secondary magnetic signals received back from a stimulated sample. The first is based on using a resonator circuit and coupled coil, and sensing received signals based on changes in the resonance frequency of the circuit. The second is to sense the received signals as small voltages induced in a dedicated receiver coil.

All known resonator-based inductive sensors use a single loop for both generating the primary magnetic field and for picking up the secondary magnetic field. Known devices which operate by sensing the signals as induced voltages by contrast use separate transmission coil(s) and receiver coil(s); known devices using a dedicated transmission and receiver coil do not operate by sensing resonance frequency changes.

Inductive sensors which use a single loop for both generation and detection of magnetic fields have been found to suffer from a problem that detected signals are highly susceptible to motion artifact (distortions in the data which arise when the sensor is moved relative to the body being probes. This can be understood as arising for the following reasons. The strength of generated secondary eddy currents decreases with distance from the signal generating loop. For this reason, eddy currents induced at the surface of the probed body are much stronger than those induced in the targeted deeper tissue. Surface generated currents are not in general useful for most sensing applications, only the deeper currents. Furthermore, the surface eddy-currents are naturally very close to the wire of the resonating loop and therefore strongly influence the detected signal. As a result, small changes in the distance between the loop and the tissue being probed may result in signal artefacts which are much larger in magnitude than the desired deeper tissue signals, e.g. cardiac or respiratory-related signals.

Inductive sensors based on separate transmission and receiver coils suffer from a different problem that the detected voltages in the receiving loop are extremely small and furthermore strongly dominated by direct magnetic coupling with the transmission coil. Complicated compensating circuitry must be used, such as lock-in amplifiers and heavily shielded multiplexers, in order to extract the very small sensed signals. This increases complexity, cost and form factor of such devices, and their added complexity increases possibilities for failure.

An improved induction based sensor is sought which is able to overcome the problem of motion artefacts encountered with single-coil devices, without the added circuital complexity and low pick-up strength of known two-coil solutions.

SUMMARY OF THE INVENTION

The invention is defined by the claims.

According to examples in accordance with an aspect of the invention, there is provided an inductive sensing device for inductively coupling electromagnetic signals into and out of a medium, the device comprising:

a first loop part, coupled with a capacitor to form a resonator circuit;

a second loop part;

respective conductor lines forming the first and second loop parts being radially spaced from one another along at least portions of the conductor lines; and an output of the resonator circuit being electrically connected to the second loop part via an active buffering component, the active buffering component adapted to implement voltage to current amplification, and an output of the active buffering component configured to drive an alternating current in the second loop part.

The invention is hence based on use of a weakly coupled two-loop arrangement, a first loop which is part of a resonator circuit and may predominantly be used for sensing signals, and a second loop, which is not directly part of the resonator circuit, which is actively driven, and which may be used as the predominant source of generated signals, the two being weakly coupled via an active buffering component.

The coupling provides that the two loops operate synchronously: with currents of the same frequency and in phase with one another. This ensures co-operative behavior, with one loop not causing noise in signals of the other. The buffering however at the same time provides that the two loops are partly isolated electrically. In particular, the isolation is one-way: the first loop being isolated from fluctuations in the current in the second. In this way, magnetic fields sensed at the second (driven) loop do not affect the resonator frequency; only magnetic fields sensed at the first (resonator) loop affect the resonator frequency.

As a result, a signal output of the resonator circuit can be used a sensing output for the device (e.g. for deriving physiological measurements), unaffected by fluctuations in the second loop. This obviates the above mentioned problems of two-loop configurations in which the driving loop interferes with the sensed signals at the resonating loop.

Furthermore, the amplification provided by the buffering component ensures that currents in the second loop part are stronger than those in the first loop part. This means that the second loop part is the dominant source of transmitted magnetic signals (magnetic fields directed into the tissue), and also the dominant driving source of secondary eddy currents induced at the tissue surface.

As noted above, surface eddy currents predominantly cause motion artefacts due to their inevitable closeness to the conducting line (wire) of loop which stimulates them. However, in the present arrangement since the first and second loop parts are at least partially radially spaced, the predominant surface fields are always radially closest to the second loop, and hence affect only the second loop in a significant way. However, due to the buffering of this (second) loop from the main resonating loop (the first loop), any fluctuations in the second loop do not affect the frequency in the resonator circuit. Hence the signal output of the resonator circuit remains far less affected by secondary surface eddy currents than in known devices.

Fluctuations in the second loop are furthermore quickly overcome by the active driving which provides a strong forcing which overpowers any surface artefacts.

The at least partial radial spacing (i.e. spacing along at least sections of the loops) also minimizes direct coupling between the two loops (direct coupling occurring only where the conductive line of one loop exactly overlaps or overlies that of the second loop). This avoids the problem of the sensing signal in the first loop being dominated by direct coupling from the second (or vice versa). Sensitivity and signal quality is thereby enhanced.

In summary, the benefit of the device of the present invention can be summarized as follows:

the amplification provided by the buffering element means that the second loop is the dominant source of surface eddy currents;

the spacing between the two loops means that these dominant surface eddy currents affect only the second loop in a significant way;

the buffering between the two loops means that the effect of the surface eddy currents on the second loop is substantially isolated from affecting the resonator frequency (whose output provides the measuring signal);

however, the weak coupling via the buffering element ensures that the two loops operate synchronously, which avoids the problem associated with known two-loop solutions of only a very weak measuring signal being detectable (atop a large background signal) due to the target reflected signals only being picked up by one of the loops. Instead, the synchronicity means that the target reflected signals are picked up by the total system of both loops. In particular, the signal can be measured as a change in frequency and/or amplitude of the total, combined system of the two synchronous loops. This thereby avoids the need for complicated compensatory electronics such as lock-in amplifiers or shielded multiplexers.

In this way the novel buffered coupling arrangement provided by the present invention significantly reduces surface artefact effects, and hence sensitivity of the device to movement, while at the same time avoiding the various difficulties associated with known two-loop arrangements.

The frequency in the controlled loop is determined by the output of the amplifier (the active buffering component), while, at least in some examples, the resonating loop may effectively perform as a freely running oscillator, its frequency determined by the pickup of magnetic fields in the resonating loop.

The sensing device finds advantageous application for sensing electromagnetic signals emitted from a medium in response to propagation into the medium of electromagnetic excitation signals. The excitation signals are generated by a combination of the first and second loop parts, the second loop part providing the dominant source. Resonating of the first loop is preferably driven via magnetic coupling with the second loop, the second loop being actively driven (by the active buffering component).

Holding the antenna in proximity to a medium, such as a body, the signals are inductively coupled into the medium, and induced electromagnetic response signals are (typically simultaneously) coupled back out and into the resonator (first) loop. This mutual coupling induces changes in the electrical characteristics of the current in the first loop which can be detected to derive properties of the stimulated medium.

Hence the first loop may effectively act as a sensing loop. The second loop may effectively act as a driving (or transmitting) loop.

For the avoidance of doubt, radially spaced means spaced or spatially separated or spatially offset in a direction parallel with the plane defined by the respective loop. Hence, at least portions of the conductive lines defining each of the first and second loop parts may be spaced or separated in a direction parallel with the plane defined either the first or the second loop. The loops do not fully radially overlap or overlay one another in this case. There is in this case a non-zero average radial spacing between the conductive lines of the two loops. The conductive lines of the two loops are radially offset from one another, or at least partially radially offset.

In some examples for instance, the first loop part may have a smaller radius that the second, and be radially inset within the second (or vice versa).

In other examples, the loops may be fully separated from another in a radial direction, with no overlap of the wires at all.

In further examples, the loops may partially overlap, with the conductive lines of the two loops crossing at one or more points, but wherein there is not exact or complete radial overlap of the conductive wires of the loops, i.e. the loops are radially offset from one another. For examples, respective interior areas defined by each of the first and second loop parts may partially overlap, such that the conductive lines of the first and second loop parts cross at two or more points.

This arrangement carries additional advantages in that disruptive direct coupling between the loops can be minimized where the conductive line of one loop passes close to a central point or region of the interior area encompassed by the other loop. This means that the gain of the buffer amplifier can be enhanced without risk for instance of uncontrolled or runaway amplifier amplitude due to direct coupling of the loops. This enhanced gain is beneficial, so as to maximize the current in the second (transmitting) loop part compared to the first (sensing) loop part (so that the second loop dominates in terms of transmitted signals).

Each loop part may be a (complete) closed loop part, i.e. each loop part forms or defines a respective closed loop. These respective closed loops are separate. The loops are each formed of at least one conductive line which defines the loop.

Buffering components are a well-known class of electrical component, and the skilled person will be aware of means for implementing such a component. Buffering components are otherwise known in the art as buffer amplifiers, or simply buffers. For example, in the present case, a buffer adapted to implement voltage to current amplification is used. In general, a buffering component is an electrical component that provides electrical impedance transformation from one circuit (or portion of a circuit) to another, with the aim of preventing the signal source from being affected by whatever currents (or voltages, for a current buffer) that the load may produce. The signal is 'buffered from' load currents. Two main types of buffer exist: the voltage buffer and the current buffer.

The first loop part is preferably arranged in magnetic coupling relationship with the second loop part (i.e. arranged such as to magnetically couple with the second loop part) such that, in use, the driving of the current in the second loop part by the active buffering component magnetically induces a synchronous current in the first loop part.

Synchronous means synchronous with the current of the second loop part, e.g. the first and second loops oscillate with currents of a common frequency. The currents of the two loops may be in phase with one another, or with a fixed phase delay or phase offset (i.e. the frequencies are locked).

This arrangement carries the advantage that the oscillating of the first (resonator circuit) loop does not require a dedicated damping compensation circuit (e.g. an active oscillator) in order to maintain or initiate oscillating of the resonator. Instead, the resonator oscillates because of the magnetic coupling with the second loop, which is driven by the active buffering component. As a result, power consumption and device cost is reduced, for example due to the reduction in the number of components.

Furthermore, it provides the further benefit that synchronization between the first and second loops is established immediately as the device begins to operate (as opposed to the short delay that would otherwise ensue as synchronization stabilizes via the weak buffered coupling).

In addition, the absence of an active driving component for the resonator loop minimizes sensitivity of the device to electrical fields, while the magnetic field sensitivity remains. This is because an active driving component, such as a driving oscillator, or other damping compensation element, typically introduces parasitic capacitances to the resonator. Such parasitic capacitances are sensitive to electric fields originating from capacitive coupling with any proximate objects, e.g. in this case the skin surface. Hence absence of a driving component for the resonator loop (first loop part) significantly reduces disruptive capacitive coupling with the surface of the probed body.

Each loop part may be formed by a single-turn loop.

Keeping the number of windings small advantageously minimizes capacitive effects between the wires forming each of the loops. However a single winding is not essential and one or both loop parts may comprise more windings in other examples.

Each loop part may be formed of closed loop, for example a single-turn closed loop. The loop may be a loop of conducting line, e.g. a wire.

The active buffering element may be configured to drive the second loop at a frequency which matches a resonance frequency of the resonator circuit. The active buffering component does not actively set a frequency at which the second loop oscillates, but rather is arranged to amplify a received output of the first (resonator) loop part, this amplified signal being provided as the driving signal for the first (transmitting) loop part.

It is noted that upon first activating the sensing device, there are not yet any oscillating currents in the resonator loop (first loop part). However, there will always be some small noise fluctuations in the first loop part. The electrical configuration ensures that upon activation of the amplifier, the amplification of these fluctuations quickly leads to initiation of oscillation of the two loop parts. In particular, the amplitude will rapidly increase until the loop gain reaches 1. Furthermore, the weak coupling arrangement between the coils results in stabilization of the system at a state of synchronous currents in both loops, and with zero or fixed phase delay. The mode (frequency, amplitude) at which the system starts oscillating will be one at which the Barkhausen stability criterion is met.

According to one or more embodiments, the inductive sensing device may further include an adjustable or tuneable phase delaying element connected between the active buffering component and the second loop part. The adjustable phase delaying element applies an adjustable (e.g. user-adjustable or automatically adjusted) phase delay to the signal output of the active buffering component in advance of supplying the output to the second loop part.

This may for example allow any phase latencies, e.g. induced by the active buffering component, or the connection to the second loop, to be compensated. In particular, the phase delaying element may be configured to apply a phase delay such that the output signal provided to the second loop part is in-phase with the oscillations (i.e. the current) of the first loop part (or with a fixed phase offset of $2\pi$ or a multiple thereof). This is advantageous, since for oscillations in both loops to begin and to continue stably and synchronously with one another, the Barkhausen criterion should be met. This preferably requires that the oscillations (i.e. currents) of the first and second loop parts are in phase (or separated by a fixed phase delay of a multiple of $2\pi$). The phase delaying element may be dynamically adjusted (for example by a controller or processor) so as to maintain such a zero or constant phase offset.

The output of the resonator circuit may be further coupled to a signal output connector, for connection with signal processing means.

The output connector may be a terminal or coupling point for making the connection with a signal processing means. The signal processing means may be external to the provided sensing device, or may be provided as part of the device.

Only the output signal of the resonator loop is used for signal processing, for analyzing signals received from the stimulated body.

The inductive sensing device may in come embodiments comprise a damping compensation circuit electrically coupled to the resonator circuit, configured to actively compensate for damping of a current in the resonator circuit.

As noted above, preferably the resonator circuit is driven by magnetic coupling with the second loop, the second loop being actively driven by the active buffering component. However, in cases where the coupling is not sufficiently strong to provide for this, a separate component can be provided to compensate for damping in the resonator circuit, to ensure the resonator circuit continues or begins to oscillate.

The damping compensation circuit is preferably adapted to provide an active driving current to the first loop part. The active driving current may be provided at a frequency matching a (natural) resonance frequency of the resonator circuit in examples.

The damping compensation circuit may for example comprise an active oscillator.

As noted above, the spacing of the first loop part from the second loop part ensures that the dominant surface eddy currents generated by the second loop leave the first loop relatively unaffected. The spacing of the conductor lines of the two loops relative to the spacing between the loops and the probed body surface is a significant factor in this effect.

Accordingly, in advantageous embodiments, the inductive device may comprise a support structure having a tissue contact area for application to an incident tissue surface, the first and second loop parts being mounted to the support structure and orientated to output and receive magnetic signals in a direction of said contact area, and arranged such that an average spacing between respective conductor lines forming each the first and second loops is equal to or greater than a distance between the second loop part and the contact area.

Average spacing may refer to an arithmetic average of the spacing.

Average spacing for instance may be determined by summing and averaging a radial spacing between the conductive lines of the two loops around the entire periphery of the two loops. This may comprise integrating the radial spacing around the conductive lines, and dividing by the circumference of one of the loops for instance.

The first and second loops may for instance be orientated facing the contact area.

This embodiment hence configures a radial separation of the two loops (in particular between the conductive lines of the two loops) relative to a separation of at least the second loop from a probed tissue surface in use.

By positioning the wire of the first (resonating) loop sufficiently far away from the wire of the second (actively controlled) loop (at least equal to or further apart than the distance to the tissue surface), the pickup of unwanted surface fields from the surface (generated by the dominant first loop) by the resonating loop is reduced. Hence, the motion sensitivity of the sensor, which is mainly the sensitivity to variations of the unwanted secondary magnetic fields originating from the tissue surface, is further reduced.

Defining the average spacing between the loop lines takes into account the fact that the lines may not be perfectly concentric, or aligned. Hence a separation between the lines may vary at different points around the respective loop peripheries. The average spacing is the important measure.

As noted above, the device may further comprise signal processing means, an output of the resonator circuit being coupled to the signal processing means, and the signal processing means being adapted to determine a measure of one or more physiological parameters, based on the signal output.

In particular, the signal processing means is preferably configured to analyze a (resonance) frequency of the resonator circuit, and determine a measure of the physiological parameter based on said frequency.

Alternatively, the signal processing means can be configured to analyze an oscillation amplitude of the resonator loop (the first loop part) and determine a measure of the physiological parameter based on said amplitude.

According to one or more embodiments, the capacitor of the resonator circuit may have a controllable capacitance. This increases flexibility of the device, as the resonating frequency of the resonator circuit can be tuned or adjusted or configured to suit different particular applications.

According to one or more advantageous embodiments, the device may comprise a further capacitor, coupled to the second loop part.

This adds a secondary benefit of reduced heat dissipation in the active buffering component. In particular, during back-and-forth reversal of the current in the second loop part, the energy of the magnetic field of the second loop part is temporally stored in the capacitor every oscillation cycle. This reduces heat dissipation in the voltage to current amplifier.

The further capacitor may advantageously be configured with a capacitance of a value so as to define an oscillating frequency of the second loop part which matches a natural oscillating frequency of the first loop part.

By tailoring the capacitance of the capacitor for the second loop (for example via control by a microprocessor) such that the second loop is operated at or close to the natural oscillation frequency of the first loop part, the heat dissipation in the voltage to current amplifier is brought to a minimum. This is especially advantageous in applications where low power consumption is important (e.g., for wearable inductive sensors with a limited battery capacity.

In the absence of the capacitor, the amplifier would be required on each cycle to exert forcing such as to force the received frequency from the first loop into the resonance frequency of the second loop (i.e. to overcome the disparity between them). This would generate heat and consume power.

The natural oscillation frequency means the electrical self-resonance frequency. The second loop in the absence of a capacitor typically has a very high natural frequency. By adding a tuning capacitor, the radial frequency may be reduced, in particular by an amount $\omega_0 = (LC)^{-1/2}$, where L is the inductance of the loop and C is the total capacitance of the loop and the added tuning capacitor. It may be reduced such that the natural frequency of the second loop is close the natural frequency of the first loop. The required work of the amplifier is thereby reduced, and power consumption correspondingly reduced.

The further capacitor for the second loop part may have a controllable capacitance.

This increases flexibility of the device, since the second loop can be configured for instance to match different possible resonance frequencies of the resonator circuit.

The capacitance of the capacitor may be dynamically adjusted (for example with a processor or controller) such as to maintain an operating frequency of the second loop part substantially matching that of the first loop part.

The device may be configured such that the first and second loop parts occupy a common plane. This is advantageous because such an arrangement minimizes form factor.

For example, the device may comprise a support part, or a support structure, to which the first and second loop parts are mounted. The support part may then have the first and second loop parts arranged occupying a common plane.

The first and second loop part may furthermore be inset within the other (i.e. one loop is arranged inside the other). This naturally requires that one loop has a smaller radius than the other. Preferably the second loop part is inset within the first. Hence the first and second loops form a nested loop arrangement. For example, the two loops may each define (delineate) an interior area, and wherein the interior area of one loop is fully enclosed within the interior area of another. For example, one loop may have a smaller radius, and have an interior area which fully overlaps with an interior area of the other (larger radius) loop.

A nested arrangement such as this advantageously saves space. In this case the radial spacing between the respective conductive lines of the two loops may be provided by the disparity in radius of the two loops.

According to one or more examples, respective interior areas defined by each of the first and second loop parts may be arranged to partially overlap, such that the conductive lines of the first and second loop parts cross at two or more points. The loops may in this case be partially overlapping and partially non-overlapping.

Examples in accordance with a further aspect of the invention provide an inductive sensing method comprising coupling electromagnetic signals into a medium, the method making use of a loop arrangement comprising:

a first loop part, coupled with a capacitor to form a resonator circuit, and a second loop part, respective conductor lines forming the first and second loop parts being radially spaced from one another, and an output of the resonator circuit being electrically connected to the second loop part via an active buffering component adapted to implement voltage to current amplification, and the method including driving an alternating current in the second loop part by means of an output of the active buffering component.

Options and embodiments described above in relation to the device aspect of this invention may be applied with equal advantage to the above-outlined method aspect of the invention.

According to one set of advantageous embodiments, the method comprises holding said loop arrangement relative to a surface of a medium to be investigated, such that a distance from the second loop part to the medium surface is equal to or less than a minimum spacing between the conductive lines of the first and second loop parts.

This hence provides the advantageous relative spacing arrangement described above, wherein a minimum spacing between the loop parts and the probed surface is less than or equal to a spacing between conductive lines of the loops themselves. Again the spacing between the conductive lines may be defined by a support structure to which the loops are mounted, or may be defined by a configuration in which a user holds the device.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
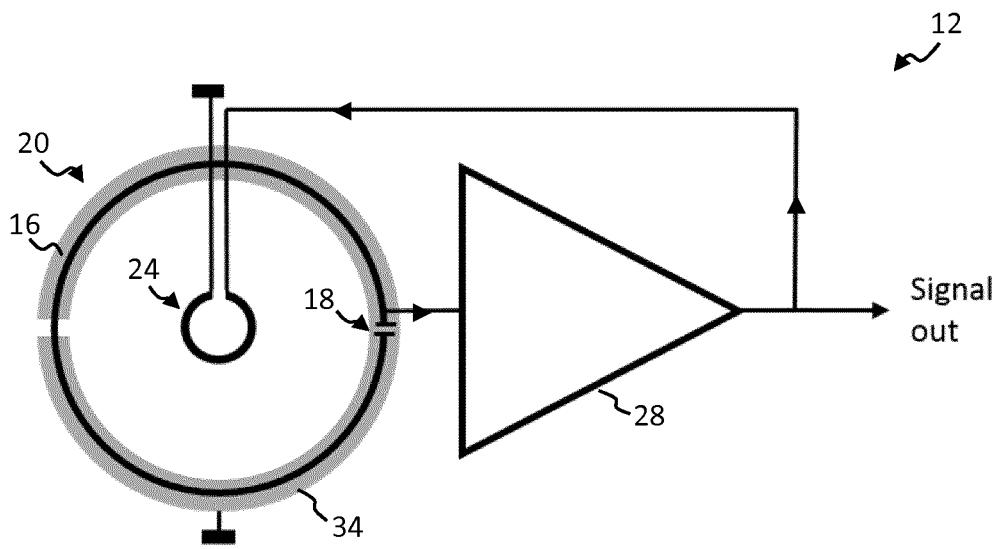
FIG. 1 shows an example inductive sensing device according to one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an inductive sensing device comprising first and second loops, the first loop being coupled with a capacitor to form a resonator circuit, and the resonator circuit and second loop being coupled via an active buffering component. The active buffering component provides voltage to current amplification, and an output of the buffering component drives a current in the second loop. Conductive lines forming each of the first and second loop parts are spaced apart radially.

In advantageous examples, the second loop part has a smaller radius that the first and is inset within the first.

Recent innovations in the field of inductive sensing have enabled simple contactless measurements of mechanical activity of internal anatomical structures such as the heart and the lungs. Such sensors may advantageously be implemented in wearable patient monitors, contactless patient monitoring, and also for rapid spot-check measurements.

The working principle of inductive sensing is based on Faraday's law. An oscillating primary magnetic field is generated by a generating loop, and this induces, via Faraday's law of induction, eddy currents in the probed tissue. The eddy currents generate a secondary magnetic field, which is detected by a pick-up loop. As for instance breathing, heart contractions, and aortic or other arterial dilations alter the geometry of the conductive structures being probed, these also alter the eddy currents, and hence the secondary magnetic field. This can hence be detected in the signal that is sensed by the pick-up loop.

Recent developments have for example greatly improved the signal strength by shifting the operating frequency to a novel range of 50-500 MHz, and by shielding the electronics from electrical disturbances in a sophisticated manner. It has been found by the inventors that inductive sensors that operate with a single loop as part of a resonator provide the strongest signal-to-noise ratio.

As noted above, a deficiency in known single-loop sensors is very great sensitivity to motion artefacts, caused by dominant surface eddy currents. The inductive sensing device of the present invention substantially obviates this problem.

In summary, the benefit of the device of the present invention can be summarized as follows:

the amplification provided by the buffering element means that the second loop is the dominant source of surface eddy currents;

the spacing between the two loops means that these dominant surface eddy currents affect only the second loop in a significant way;

the buffering between the two loops means that the effect of the surface eddy currents in the second loop is isolated from affecting the resonator frequency (whose output provides the measuring signal);

however, the weak coupling via the buffering element ensures that the two loops operate synchronously, which avoids interference between the two loops; in particular, it is avoided that the resonator frequency is dominated by out-of-phase magnetic signals coupled from the dominant second loop.

FIG. 1 illustrates an example inductive sensing device 12 in accordance with one or more embodiments of the present invention, the device being for inductively coupling electromagnetic signals into and out of a medium.

The inductive sensing device 12 comprises a first loop part 16 and a second loop part 24. The first loop part is coupled with a capacitor 18 to form a resonator circuit 20. The resonance frequency of the resonator circuit is (at least in part) defined by the capacitance of the resonator circuit.

Each of the first and second loop parts is formed of a closed, single turn loop of a conductive line, e.g. a wire.

The respective conductor lines of the first 16 and second 24 loop parts are radially spaced from one another. In the example of FIG. 1, the radial spacing is facilitated by the second loop part having a smaller radius that the first loop part and being arranged inset within the first, i.e. inside the first. For instance the respective interior area of the second loop part 24 is fully contained within the interior area of the larger radius first 16 loop part. However, this specific arrangement is not essential (as will be outlined further below). In this example, the two are occupy a common plane, but this is also not essential, and the two may alternatively be axially displaced from one another for instance.

An output of the resonator circuit 20 is electrically connected to the second loop part 24 via an active buffering component 28. The buffering component provides a buffering function, which implements a one-way electrical isolation of the resonator circuit from the second loop part, such that the resonator circuit 20 is isolated from electrical fluctuations in the second loop part 24.

The active buffering component 28 is further adapted to implement voltage to current amplification, and an output of the active buffering component is for driving an alternating current in the second loop part 24.

As noted previously, buffering components are a well-known class of electrical component, and the skilled person will be aware of means for implementing such a component. Buffering components are otherwise known in the art as buffer amplifiers, or simply buffers. For example in the present case, a buffer adapted to implement voltage to current amplification is used. In general, a buffering component is an electrical component that provides electrical impedance transformation from one circuit (or portion of a circuit) to another, with the aim of preventing the signal source from being affected by whatever currents (or voltages, for a current buffer) that the load may produce. The signal is 'buffered from' load currents. Two main types of buffer exist: the voltage buffer and the current buffer.

In the present case, the first loop part 24 is buffered from fluctuations in current in the second loop part. The second loop part can hence be understood the 'load' in this case.

The active buffering component 28 may comprise a voltage buffer connected to a voltage to current amplifier, to thereby implement the buffering and amplification functions. The voltage to current amplifier is beneficial as it assists in generating the current required for oscillating the second loop part (the transmitting loop).

In some examples, the active buffering component 28 may comprise an operational amplifier connected to a voltage-to-current amplifier.

In the shown example, the first loop part, and encompassing resonator circuit, is further provided with an electromagnetic shielding element 34 arranged to provide shielding of the first loop part and the capacitor 18 from electric fields. The shielding element may for instance be a shielding plate or body. It may be formed of a metal. It may delimit one or more slits or openings through the body of the element, to inhibit formation of eddy current in the shielding element, and therefore interfering magnetic fields. The shielding element however is optional, and not intrinsically linked to the functioning of the sensing device.

The shielding element 34 is optionally grounded, as shown in FIG. 1, while the resonator circuit 20 is ungrounded. The shield 34 and first loop part 16 are separated by an insulative spacing medium, such as a dielectric layer.

An output of the active buffering component 28 is further coupled to a signal output connector 30 for connection to signal processing means. Optionally, the inductive device 12 may include signal processing means for analyzing a frequency of the resonator circuit, and based on this deriving a measure of one or more physiological parameters.

In use, resonator 20 output signals at said output connector 30 may be analyzed by a signal processing means (including for example control and readout electronics). Information about the probed body, for example cardiac and/or respiratory information will be present in the resonator oscillation frequency, which may be measured by the signal processing means. In particular, information concerning the probed medium may be detectable as variations in the frequency of the resonator circuit.

A cardiac pulse for instance may be visible as small but clearly detectable variations in the resonator circuit 20 frequency, and breathing may be detectable as larger, slower variations in the resonator circuit 20 frequency.

In the example of FIG. 1, the device is configured such that the first and second 24 loop parts occupy a common plane, and furthermore such that second 24 loop part is smaller than, and inset within, the first loop part. This provides a space-compact arrangement.

Figure 2:
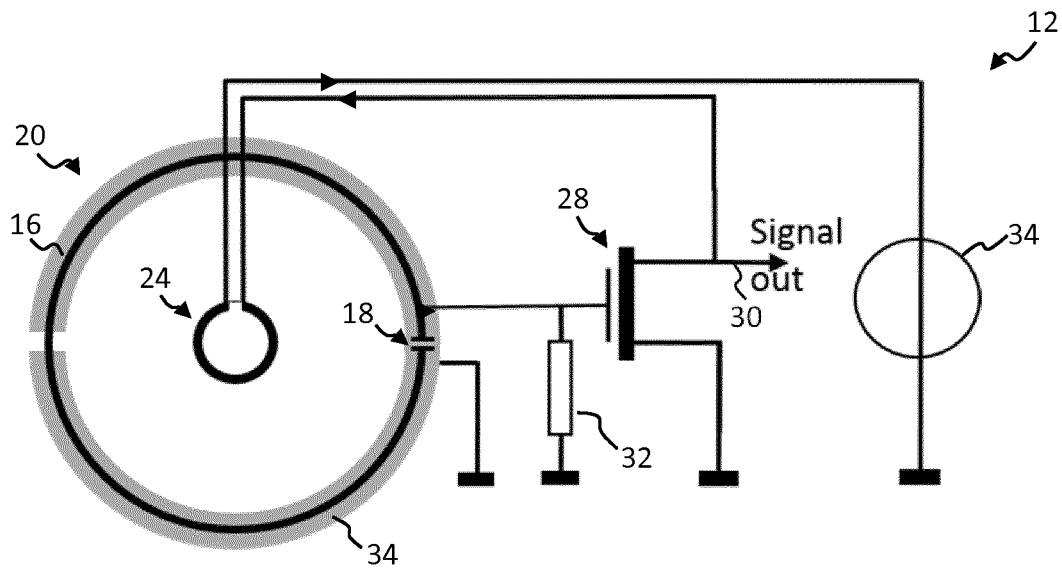
FIG. 2 shows the circuit arrangement of the example sensing device of FIG. 1 in greater detail.

FIG. 2 shows the circuit arrangement of the example inductive sensing device of FIG. 1 in more detail.

The active buffering element 28 is illustrated. The voltage to current amplification is provided in combination with buffering between the resonator circuit 20 and the second loop part 24.

As discussed in the previous section, in a preferred embodiment, the first 16 and second 24 loop parts are arranged in magnetic coupling relationship (i.e. the first loop arranged so as to magnetically couple with the second loop), such that, in use, the driving of the current in the second loop part by the active buffering 28 component magnetically induces a synchronous current in the first loop part. Such magnetic coupling relationship can be achieved by a wide range of different relative spatial arrangements of the loops. In the examples of FIGS. 1 and 2, the loops are arranged in-plane and nested within one another. However, and as discussed in more detail below, magnetic coupling can also be achieved in examples in which the loops are arranged adjacent, i.e. side-by-side, one another.

Such an arrangement delivers secondary advantages, in that it does not require presence of a damping compensator (such as an active oscillator) coupled with the resonator circuit 20 in order to initiate and/or maintain oscillation of the resonator. Instead, the resonator oscillates due to the magnetic coupling with the second loop, which is driven by the active buffering element 28.

The advantages of the optional absence of a dedicated damping compensator include firstly that a dedicated oscillator driver for the resonating circuit is not needed which saves power and reduces costs due to reduction in parts. In addition, synchronization between the first 16 and second 24 loops is established immediately as the resonator begins to oscillate, as opposed to there being a small delay as synchronization is stabilized via the buffered coupling of the loops. Furthermore, electric field sensitivity is minimized while the sensitivity to magnetic fields remains.

This is because an active driving component, such as a driving oscillator or other damping compensation element, typically introduces parasitic capacitances to the resonator. Such parasitic capacitances are sensitive to electric fields originating from capacitive coupling with any proximate objects, e.g. in this case the surface of a body being probed. Hence absence of a driving component for the resonator loop (first loop part) significantly reduces disruptive capacitive coupling with the surface of the probed body.

Electric fields are not useful for the inductive sensing, and introduce noise in the sensed signal.

Use of magnetic feedback to begin oscillation has been used in previous unrelated fields, for instance with so-called Armstrong oscillators. However, this principle has never been applied in the context of an inductive sensing device, as in embodiments of the present invention. In particular, for known Armstrong oscillators, sensitivity to inductive and capacitive coupling with external bodies is considered detrimental, and the circuit is configured to minimize such coupling. By contrast, for embodiments of the present invention, magnetic coupling with external bodies is the object of the device.

Hence in embodiments of the present invention, there may advantageously be used in some examples relatively large, optionally electrically shielded, single-winding loops. By contrast, known Armstrong oscillators typically comprise small multiple-winding coils.

For example, for inductive sensors according to embodiments of the present invention (e.g. for the purpose of vital-sign monitoring) typical loop diameters may be between 1 cm and 5 cm. In general, the loops may have a diameter greater than around 1 cm. The loops preferably have one winding only. Loops of diameter greater than 1 cm and with a single winding would not be beneficial for use in Armstrong oscillators, since this would render the electronics prohibitively bulky and also lead to increased coupling with external bodies, which is disadvantageous for Armstrong oscillators.

The described magnetic coupling relationship is not essential to the invention. The benefits of the inventive concept are not inextricably linked with such a feature. As an alternative, a dedicated damping compensation circuit may instead be provided for example, for the purpose of initiating or maintaining oscillation in the resonator circuit 20. An oscillator may be provided for initiating and/or maintaining oscillation of the resonator circuit for example.

FIG. 2 schematically depicts such an optional damping compensation circuit 32, electrically coupled to the resonator circuit 20, configured to actively compensate for damping of a current in the resonator circuit. The damping compensation circuit may in examples comprise an oscillator circuit.

If for example direct magnetic coupling between the second (driven) loop 24 and the first (resonating) loop 16 is too weak or too unstable for the resonator circuit 20 to start oscillating via this coupling alone, then the circuit may be made more robust by provision of a dedicated damping-compensation circuit 32 electrically coupled with the resonator circuit. The device in this case no longer depends upon the direct magnetic coupling between the second loop 24 and the first loop 16.

According to one set of advantageous embodiments, the circuit of the example inductive sensing device may further include an adjustable or tuneable phase delaying element connected between the active buffering component 28 and the second loop part 24. The adjustable phase delaying element applies an adjustable (e.g. user-adjustable) phase delay to the signal output of the active buffering component 28 in advance of supplying the output to the second loop part.

This may for example allow any phase latencies, e.g. induced by the active buffering component 28 or the connection to the second loop, to be compensated. In particular, the phase delaying element may be configured to apply a phase delay such that the output signal provided to the second loop part is in-phase with the oscillations (i.e. the current) of the first loop part (or with a fixed phase offset of $2\pi$ or a multiple thereof). This is advantageous, since for oscillations in both loops to begin and to continue stably and synchronously with one another, the Barkhausen criterion should be met. This preferably requires that the oscillations (i.e. currents) of the first and second loop parts are in phase (or separated by a fixed phase delay of a multiple of $2\pi$).

In use, the first 16 and second 24 loop parts of the device 12 are held in proximity to a body or medium of interest, and the second loop part is driven by the active buffering component, this then initiating oscillation of the resonator circuit 20 via magnetic coupling in the preferred examples. Both the second loop part and first loop part of the resonator circuit generate excitation signals which are directed into the tissue being probed. As noted above, the second loop part 24 provides the dominant source of transmitted, or stimulus, signals, by virtue of the higher amplitude current in this loop due to the amplification provided by the active buffer component 28.

Signals from both loops enter the tissue being probed. The second loop part dominates the eddy currents induced in the probed tissue. The induced eddy currents generate secondary magnetic fields. These secondary fields are sensed by both the second loop part 24 and the resonator circuit 20. However, the pickup strength is far greater in the resonator circuit 20 by virtue of the resonance effect (which effectively amplifies induced inductance signals in the first loop 16 of this circuit). Although pick-up strength is greater in the first loop, sensitivity to motion-artefacts (i.e. movement of the loop relative to the surface) is far greater in the second loop, due to the great radial proximity of the second loop to the dominant surface eddy current signals.

Furthermore, only signals sensed at the first loop part (the resonator circuit) are used for signal measurement, these being provided to an output connector 30 of the arrangement. In particular, signals sensed at the resonator circuit cause variations in the oscillation frequency of the resonator which can be sensed by signal processing electronics. The signals sensed at the first loop part are prevented from affecting the frequency of the first loop part by the buffering component 28. Furthermore, any variations induced in the current of the second loop 24 are actively overpowered by a forcing applied by the amplifying buffer component, which maintains a stable current frequency in the second loop. Hence signals sensed at the second loop are effectively discounted or discarded, and are not used for measurement.

In accordance with advantageous examples, the inductive sensing device 22 may be used for sensing physiological parameters and properties, for instance air, fluid and/or tissue movements in the body of a subject. The system may be advantageously applied in particular for sensing breathing movements for instance.

In these examples, the device permits sensing of air, fluid and/or tissue movements (e.g. caused by breathing or the beating of the heart) by sensing modulations in the reflected inductance of the signal caused by these movements.

According to one or more embodiments, the device may comprise a support structure for mounting the components in a particular advantageous arrangement.

Figure 3:
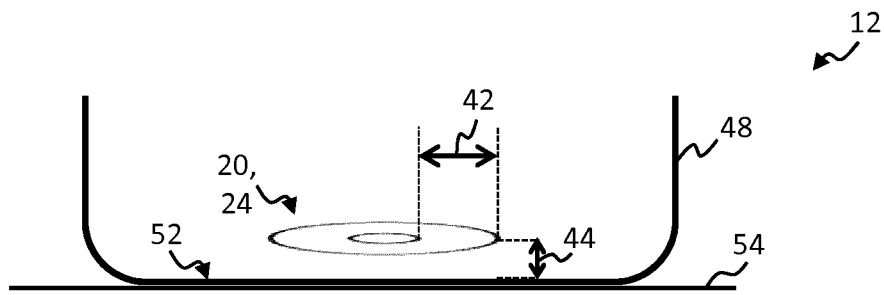
FIG. 3 schematically depicts an example support structure housing an example sensing device according to one or more embodiments.

FIG. 3 shows an example inductive sensing device 12 comprising a support structure in the form of a housing 48 within which the first and second loop parts (and the coupled circuit arrangement of FIGS. 1 and 2) is mounted. The housing 48 has the first 16 and second 24 loop parts mounted in a defined spatial configuration relative to a tissue contact area 52 of the housing. The tissue contact area is formed by a floor or base of the housing, and comprises an outer contact surface for application to an incident tissue 54 (or other e.g. non-organic body) surface. The loops are shown only schematically, and the circuit arrangement is not depicted.

The first 16 and second 24 loop parts are mounted within the housing 48 oriented facing the tissue contact area 52, so as to output and receive magnetic signals in a direction of said contact area. A radial spacing 42 between conductor lines forming the first 16 and second 24 loops is equal to or greater than a distance 44 between the second and first loops and the tissue contact area.

As noted above, in accordance with any embodiment of the present invention, the inductive sensing device 12 may further comprise signal processing means arranged to receive, as input, an output of the resonator circuit 20. The signal processing means may be adapted to derive one or more physiological parameters based on sensed signal characteristics of the received resonator circuit output. These may for instance include one or more vital signs, such as for example heart rate, pulse rate, breathing capacity, breathing rate, stroke volume, stroke volume variations, cardiac output, or aortic or arterial pulse height/pressure/diameter modulations.

The device may be a physiological inductive sensing device for sensing one or more physiological parameters of a body of a subject. The physiological parameters may include by way of example one or more of the vital signs noted above.

Preferably, the signal processing means is configured to determine a measure of one or more physiological parameters based on detected variations in an oscillating frequency of the resonator circuit.

The specific means used to implement to the signal processing is not essential to the invention. By way of example, the signal processing may comprise for instance a phase locked loop (PLL) base signal analyzer. Any other signal processing means as will be apparent to the skilled person may alternatively or additionally be used.

According to one or more examples, the sensing device 12 may optionally comprise a further capacitor, coupled to the second loop part 24. This provides an advantage in terms of reduced heat dissipation of the active buffering component 28. In particular, during back-and-forth reversal of the current in the second loop 24, the energy of the magnetic field of the second loop is temporally stored in the capacitor during each oscillation cycle. This reduces heat dissipation in the voltage to current amplifier.

For example, the capacitance of the capacitor for the second loop 24 may be selected or configured, for example by a microprocessor, such that the second loop is operated at or close to the oscillation frequency of the first loop part 16. In this case, heat dissipation on the active buffering component 28 is minimized. This is especially advantageous for example in applications where low power consumption is important (e.g., in the case of wearable sensors with a limited battery capacity).

In some examples, the capacitor for the second loop part may be an adjustable or tuneable capacitor, having an adjustable or controllable capacitance. The capacitance of the capacitor may be dynamically adjusted (for example with a microprocessor) such that an operating frequency of the second loop part substantially matches that of the first loop part.

In the absence of a capacitor, the active buffering component may be required on each cycle to exert forcing such as to compensate for the disparity between the two frequencies of the loops. This would generate heat and consume power.

An adjustable capacitor, e.g. dynamically adjustable capacitor, on the second loop part allows the natural frequency of the second loop to be close the natural frequency of the first loop. The required work of the active buffering amplifier is thereby reduced, and power consumption correspondingly reduced.

The relative positioning of the first 16 and second 24 loop parts is not crucial to the invention. However, the wires of the first and second loops should be radially spaced apart (i.e. not touching). As discussed, preferably, a minimum spacing between the wires should be greater than the distance to the body surface being probed. This can be effected by a suitable housing or support structure as discussed above.

In different examples, the second loop 24 may be outside of the first loop 16 or inside the first loop for example. A number of possible arrangements for instance are illustrated by way of illustration in FIGS. 4(*a*)-(*h*). A further option (not shown) is to dispose the first loop part 16 inside of the second loop part 24.

Figure 4:
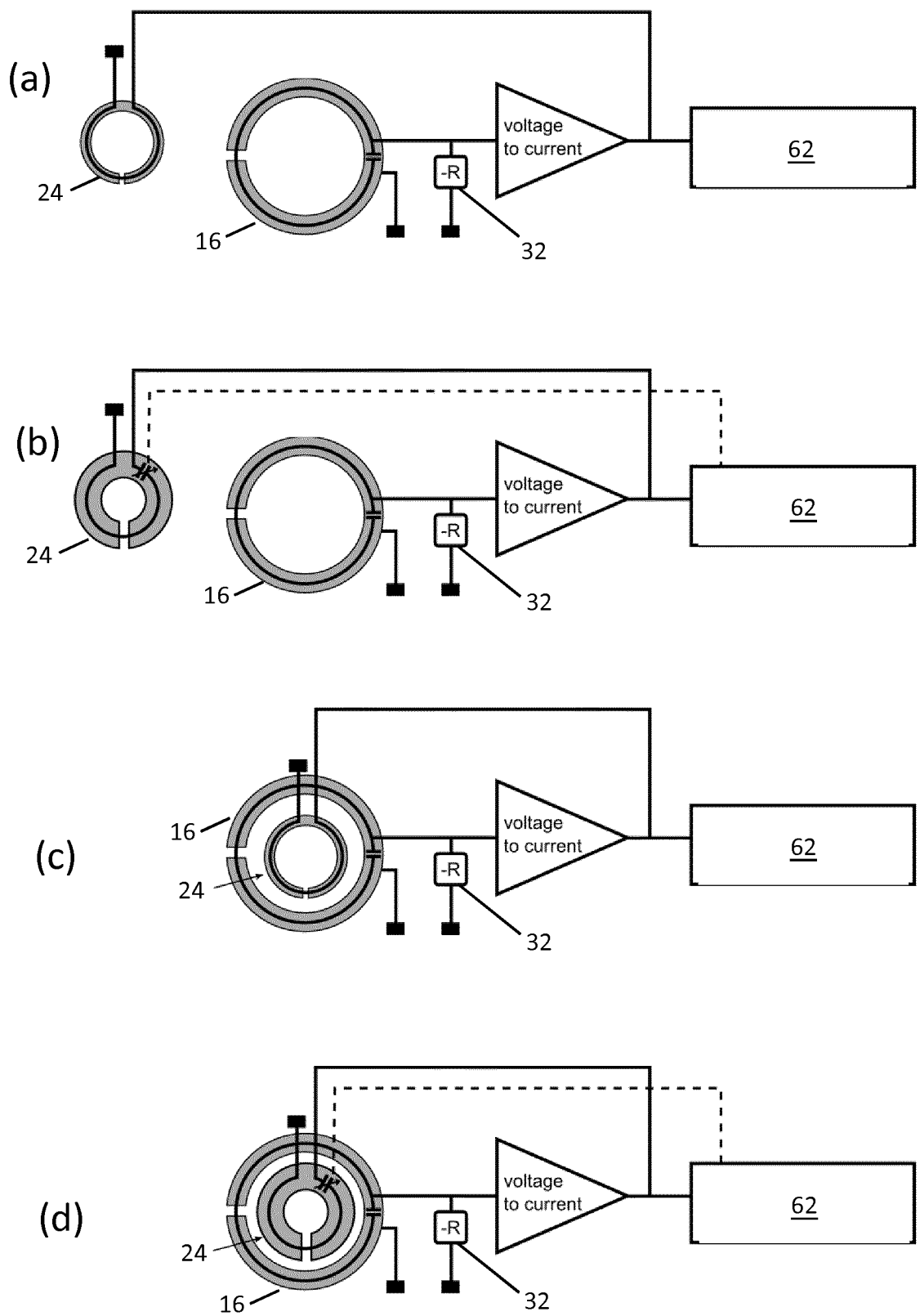
FIG. 4 shows various different arrangements for an example sensing device in accordance with various possible example embodiments.
Figure 4:
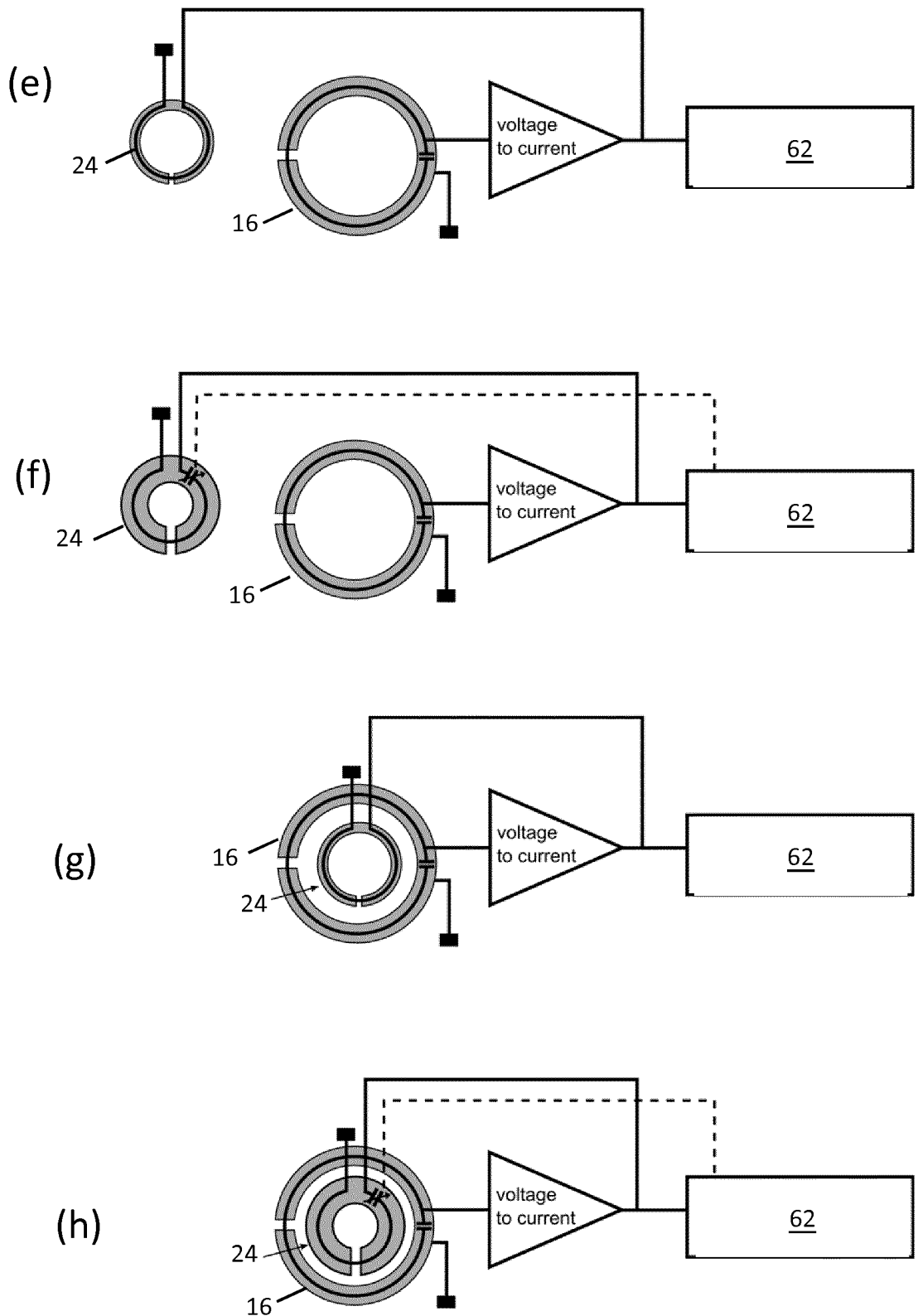

FIGS. 4(*a*)-(*d*) illustrate various arrangements, each with a damping compensation circuit 32 coupled to the resonator circuit formed by the first loop part 16. FIGS. 4(*a*)-(*d*) illustrate various options having the second 24 loop part either outside or inside the first loop part 16, and with the second loop part 24 either including or not including a dedicated further capacitor. In the case that a further capacitor is provided, this is shown electrically connected with control electronics 62 for configuring the capacitor. In this case, the capacitor has a controllable capacitance, e.g. by a microprocessor included in the control electronics. The control electronics 62 also includes signal processing means for analyzing a signal output of the resonator circuit formed by the first loop part 16, with an output of the active buffering element being coupled into the control electronics for this purpose.

It is noted that the damping compensation circuit 32 is depicted with the symbol "−R", as this component may be understood in general terms as providing an effective negative resistance, for compensating for losses in the resonator. As noted above, this may in examples be facilitated for instance by an active driving oscillator.

FIGS. 4(*e*)-(*h*) illustrate the same variations in positioning of the loops and the presence or absence of a further capacitor as in FIGS. 4(*a*)-(*d*), but simply without a damping compensation circuit provided coupled to the resonator circuit formed by the first loop part 16.

Figure 5:
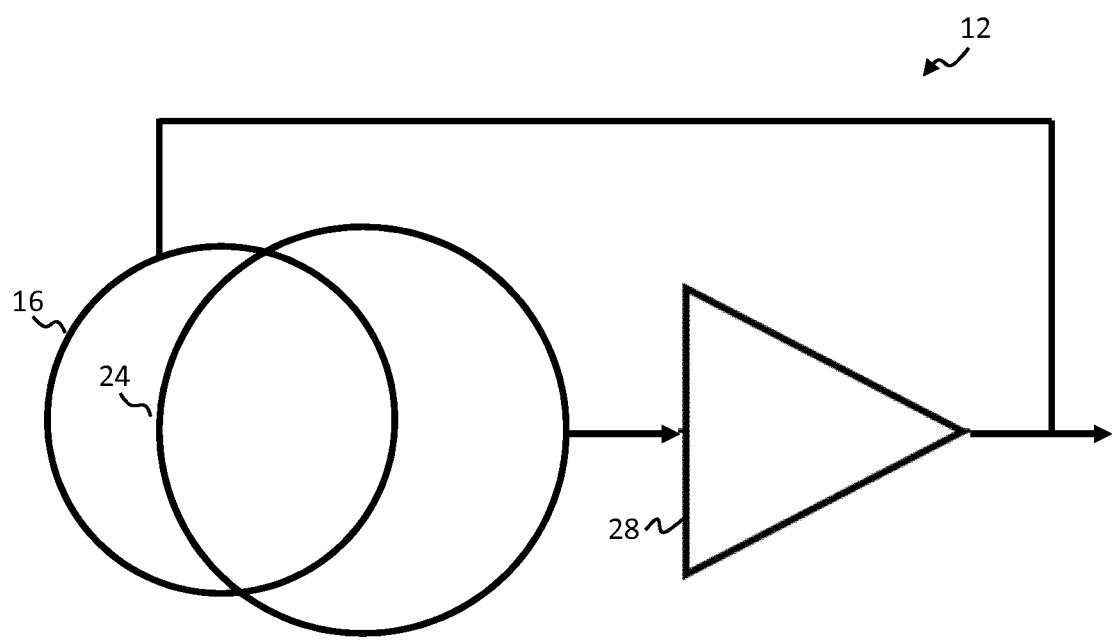
FIG. 5 shows a further example arrangement for an example sensing device, having the first and second loop parts partially overlapping.

According to a further advantageous set of examples, the first 16 and second 24 loop parts may have respective interior areas which partially overlap, such that their respective conductor lines cross at two or more points. The two loops are hence radially offset from one another. An example of this arrangement is schematically illustrated in FIG. 5.

It can be seen that in this example, although the two loops partially overlap, there is not exact or complete radial overlap of the conductive wires of the loops, i.e. the loops are radially offset from one another. The loops are partially overlapping and partially non-overlapping. Hence, the respective conductive lines of the first 16 and second 24 loop parts are not radially spaced from one another around the entire periphery of each loops part, but only across certain portions, with the respective conductor lines crossing at two points.

In the illustrated arrangement, the conductive line of each of the loops 16, 24 passes close to a central point or region of the interior area encompassed by the other loop. This carries additional advantages in that disruptive direct coupling between the loops can be minimized. This means that the gain of the buffer amplifier can be enhanced without risk for instance of uncontrolled or runaway amplifier amplitude due to direct coupling. This enhanced gain is beneficial, so as to maximize the current in the second (transmitting) loop part compared to the first (sensing) loop part (so that the second loop dominates in terms of transmitted signals).

In this example, the radial spacing between the respective conductor lines forming the first and second loop parts is non-uniform, i.e. the radial spacing varies at different points around the loops.

According to one or more examples, there may be provided a controller for controlling or coordinating inductive sensing functionality of the device. For instance this may be configured to execute a control program for operating the sensor device, optionally being responsive to input control commands received from a user or operator. There may be provided a user interface means for this purpose, such as a control interface, e.g. a control panel or touchscreen or app.

A controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Examples in accordance with a further aspect of the invention provide an inductive sensing method comprising coupling electromagnetic signals into a medium, the method making use of a loop arrangement comprising a first loop part 16, coupled with a capacitor to form a resonator circuit 20, and a second loop part 24, respective conductor lines forming the first and second loop parts being radially spaced from one another, and an output of the resonator circuit being electrically connected to the second loop part via an active buffering component 28 adapted to implement voltage to current amplification, and the method comprising driving an alternating current in the second loop part by means of an output of the active buffering component.

According to advantageous embodiments, the method may comprise holding said loop arrangement relative to a surface of a medium to be investigated, such that a distance from the second loop part 24 to the medium surface is equal to or less than a minimum spacing between the conductor lines of the first and second loops.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An inductive sensing device for inductively coupling electromagnetic signals into and out of a medium, the device comprising:
   a resonator circuit formed by a first loop part coupled with a capacitor; and
   a second loop part;
   respective conductor lines forming the first and second loop parts being radially spaced from one another along at least portions of the conductor lines; and
   an active buffering component, via which an output of the resonator circuit is electrically connected to the second loop part, the active buffering component adapted to implement voltage to current amplification, and an output of the active buffering component configured to drive an alternating current in the second loop part.

2. The device as claimed in claim 1, wherein each loop part is formed by a single-turn loop.

3. The device as claimed in claim 1, wherein the output of the resonator circuit is further coupled to a signal output connector, for connection with signal processing means.

4. The device as claimed in claim 1, the inductive sensing device further comprising a damping compensation circuit electrically coupled to the resonator circuit, configured to actively compensate for damping of a current in the resonator circuit.

5. The device as claimed in claim 4, wherein the damping compensation circuit comprises an oscillator adapted to provide an active driving current to the first loop part.

6. The device as claimed in claim 1, the device comprising a support structure having a tissue contact area for application to an incident tissue surface, the first and second loop parts being mounted to the support structure and orientated to output and receive magnetic signals in a direction of said contact area, and arranged such that an average radial spacing between conductor lines forming the first and second loop parts is equal to or greater than a distance between the second loop part and the tissue contact area.

7. The device as claimed in claim 1, further comprising signal processing means, an output of the resonator circuit being coupled to the signal processing means, adapted to determine a measure of one or more physiological parameters, based on the signal output.

8. The device as claimed in claim 1, wherein the device comprises a further capacitor, coupled to the second loop part.

9. The device as claimed in claim 8, wherein the further capacitor is configured with a capacitance of a value such as to define an oscillating frequency of the second loop part which matches a natural oscillating frequency of the first loop part.

10. The device as claimed in claim 8, wherein the further capacitor has a controllable capacitance.

11. The device as claimed in claim 1, wherein the device is configured such that the first and second loop parts occupy a common plane.

12. The device as claimed in claim 1, wherein one of the first and second loop parts is inset within the other.

13. The device as claimed in claim 1, wherein respective interior areas defined by each of the first and second loop parts partially overlap, such that the conductor lines of the first and second loop parts cross at two or more points.

14. An inductive sensing method comprising coupling electromagnetic signals into a medium, the method making use of a loop arrangement comprising:
   a first loop part, coupled with a capacitor to form a resonator circuit, and
   a second loop part,
   respective conductor lines forming the first and second loop parts being radially spaced from one another along at least portions of the conductor lines, and
   an output of the resonator circuit being electrically connected to the second loop part via an active buffering component adapted to implement voltage to current amplification, and
   the method comprising driving an alternating current in the second loop part by means of an output of the active buffering component.

15. The method as claimed in claim 14, wherein the method comprises holding said loop arrangement relative to a surface of a medium to be investigated, such that a distance from the second loop part to the medium surface is equal to or less than a minimum spacing between the conductor lines of the first and second loop parts.

* * * * *